United States Patent
Shah et al.

(10) Patent No.: US 7,722,858 B2
(45) Date of Patent: May 25, 2010

(54) PREVENTION AND TREATMENT OF ATHEROSCLEROSIS BY REDUCING CARBAMYLATION OF LDL OR THE EFFECTS OF CARBAMYLATED LDL

(75) Inventors: Sudhir V. Shah, Little Rock, AR (US); Alexei G. Basnakian, Little Rock, AR (US); Yousri M. Barri, Richardson, TX (US)

(73) Assignees: Board of Trustees of the University of Arkansas, Little Rock, AR (US); The United States of America as represented by the Department of Veterans Affairs, Washington, DC (US)

( * ) Notice: Subject to any disclaimer, the term of this patent is extended or adjusted under 35 U.S.C. 154(b) by 628 days.

(21) Appl. No.: 11/350,660

(22) Filed: Feb. 9, 2006

(65) Prior Publication Data
US 2006/0183245 A1    Aug. 17, 2006

Related U.S. Application Data

(63) Continuation-in-part of application No. 10/228,493, filed on Aug. 27, 2002, now Pat. No. 7,476,551.

(60) Provisional application No. 60/315,101, filed on Aug. 27, 2001.

(51) Int. Cl.
*A61K 49/00* (2006.01)

(52) U.S. Cl. .................. 424/9.2; 424/9.34; 435/2; 435/3; 435/967; 436/15; 436/16; 436/55; 436/71; 436/175; 436/177; 436/178; 436/506; 436/811

(58) Field of Classification Search .................. 435/7.1, 435/12, 287.2, 967, 2, 3; 436/547, 548, 506, 436/15, 16, 74, 177, 811, 507, 55, 71, 175, 436/178; 422/9.2, 9.34
See application file for complete search history.

(56) References Cited

OTHER PUBLICATIONS

Kakuk et al., DMA decreases urea-derived cyanate-induced carbamylation of serum proteins, low density lipoprotein, and haemoglobin, Nephrology Dialysis Transplantation (Jun. 2001) 16 (6): A40).*

Strongin, Sensitivity, Specificity, and Predictive Value of Diagnostic Tests: Definitions and Clinical Applications, Laboratory Diagnosis of Viral Infections, Lennette, E., ed., Marcel Dekker Inc., New York, pp. 211-219 (1993).*

Apostolov, E. et al. Quantification of Carbamylated LDL in Human Sera by a New Sandwich ELISA: *Clinical Chemistry*, 2005, vol. 51, No. 4, pp. 719-728.

(Continued)

*Primary Examiner*—Gailene R Gabel
(74) *Attorney, Agent, or Firm*—Benjamin Aaron Adler

(57) ABSTRACT

The present invention provides a method of determining whether an individual is at risk for atherosclerosis, comprising the step of measuring the level of cLDL and/or autoantibody to cLDL in a sample obtained from this individual. The invention further discloses a method of reducing carbamylation in an individual with a monomeric amino acid or other enzymatic or non-enzymatic inhibitors of carbamylation. The instant invention also provides a method to decrease the level of cLDL by direct elimination of cLDL from the blood or plasma of an individual. The invention also provides a method of treating or preventing atherosclerosis in an individual by inhibiting aggregation and/or deposition of cLDL in the individual.

8 Claims, 12 Drawing Sheets

OTHER PUBLICATIONS

Roxborough, H.E. et al. Carbamylation of Proteins and Atherogenesis in Renal Failure: *Medical Hypotheses*, 1995, vol. 45, pp. 125-128.

Ok, E. et al. Carbamylated Low-density Lipoprotein Induces Death of Endthelial Cells: A Link to Atherosclerosis in Patients with Kidney Disease: *Kidney International*. 2005, vol. 68, pp. 173-178.

* cited by examiner nLDL  cLDL  oxLDL  coxLDL 0 min    15 min    30 min    60 min    120 min    240 min Native LDL  Carbamylated LDL Native LDL  Carbamylated LDL

Normal LDL

Carbamylated LDL

PREVENTION AND TREATMENT OF ATHEROSCLEROSIS BY REDUCING CARBAMYLATION OF LDL OR THE EFFECTS OF CARBAMYLATED LDL

CROSS-REFERENCE TO RELATED APPLICATION

This is a continuation-in-part of non-provisional patent application U.S. Ser. No. 10/228,493, filed Aug. 27, 2002, now U.S. Pat. No. 7,476,551, which claims benefit of provisional patent application U.S. Ser. No. 60/315,101, filed Aug. 27, 2001, now abandoned.

BACKGROUND OF THE INVENTION

1. Field of the Invention

The present invention relates generally to the field of cardiovascular physiology and atherosclerosis. More specifically, the present invention relates to the prevention and treatment of atherosclerosis by reducing the carbamylation of LDL or the effects of cLDL.

2. Description of the Related Art

Atherosclerosis is the main cause of many cardiovascular diseases in humans. Atherosclerosis is initiated by injury to cells of the vascular wall. One group of patients that is very susceptible to atherosclerosis is patients with renal insufficiency [1-3]. Patients with end-stage renal disease (ESRD) are at several-fold increased risk of developing cardiovascular pathology because of accelerated atherosclerosis. [1,2]. Even patients with mild renal insufficiency are at 2-3-fold higher risk of cardiovascular disease [3]. The high rate of cardiovascular complications cannot be entirely explained by the known cardiovascular risk factors in these patients.

There is a large body of data which indicates that an atherosclerotic lesion starts when the vascular endothelium is injured. The injured endothelium expresses adhesion molecules for the monocytes to bind to, and the monocytes burrow beneath the endothelial cell layer, ingest modified LDL, and form so-called "foam cells". This process leads to the atherosclerotic plaque, which consists of a mass of lipid-engorged monocytes and macrophages covered by a fibrous cap being pushed out into the vessel lumen by proliferating smooth muscle cells [4-6].

When decrease renal function occurs, the increased amount of urea undergoes spontaneous (chemical, non-enzymatic) transformation to cyanate, which accumulates in patients with chronic renal failure (CRF). Cyanate acts as a potential toxin, inducing a modification of proteins called "carbamylation" [see reviews 7-9].

An example of the carbamylation reaction of free amino groups of protein N-termini is shown in FIG. 1. This reaction is 50 to 100 times faster with α-amino groups of amino acids than with ε-amino groups [7]. Isocyanic acid, the active form of cyanate, reacts irreversibly with nonprotonated groups of amino acids forming α-amino-carbamylamino acids from free amino acids. The irreversible carbamylation forming α-amino-carbamyl-lysine occurs in multiple lysine sites within a protein with accumulation over the life span of the protein. When a molecule of cyanate is removed by carbamylation, a new molecule of cyanate is formed because of the equilibrium between urea and cyanate. Reversible carbamylation occurs also at the hydroxyl groups of tyrosine, serine, or threonine, and the sulfhydryl groups of cysteine.

Very few studies have been aimed at the prevention of carbamylation, and all of them have involved lens protein [14, 15]. Incubation of rat lens in cyanate induces an aspirin-preventable increase in phase separation temperature [14]. Similarly, ibuprofen was found to induce a dose-dependent decrease in the binding of cyanate to lens protein [15]. It is possible that ibuprofen competes for cyanate binding sites. Aspirin was more effective when it was pre-incubated with lens protein, suggesting a predominantly covalent interaction. Bendazac also inhibits the carbamylation of lens protein when present with cyanate [16]. Therefore only aspirin, ibuprofen, and bendazac have been evaluated as inhibitors of carbamylation. There are no studies in which any amino acid has been used to prevent carbamylation of proteins or lipids.

The prior art is insufficient in the prevention and treatment of cardiovascular pathology caused accelerated atherosclerosis in normal individuals and deficient in the lack of an effective prevention and treatment of atherosclerosis in individuals with renal disease. The present invention fulfills this long-standing need and desire in the art.

SUMMARY OF THE INVENTION

Patients with certain diseases such as renal disease are at an increased risk of developing cardiovascular events because of accelerated atherosclerosis. The high rate of cardiovascular complications cannot be explained entirely by the known cardiovascular risk factors in these patients. There is a large body of data that indicates that an atherosclerotic lesion starts when endothelium is injured. Blood urea dissociates to form cyanate, which reacts with proteins by a process known as carbamylation. The present invention discloses that carbamylated low density lipid-cholesterol (cLDL) causes endothelial cell damage, and would thus lead to accelerated atherosclerosis and significant contribution to cardiovascular complications in patients with renal failure. An additional contributory factor is related to cLDL forming more aggregates than native LDL-cholesterol (nLDL) resulting in its deposition in the arterial wall.

The present invention discloses that lysine, glycine and arginine prevent carbamylation. The present invention further discloses that agents that inhibit or reduce carbamyation or prevent its aggregation or the effects of carbamyation provide new modalities for the treatment of cardiovascular complications in patients with renal disease. Since urea is normally present in the blood of all humans, cLDL may also play an important role in atherosclerosis in individuals with normal kidney function.

One embodiment of the instant invention discloses a method of determining whether an individual is at risk for atherosclerosis, comprising the step of measuring the level of cLDL and/or auto antibody to cLDL in a sample obtained from said individual and comparing it with the level of cLDL or auto antibody to cLDL in a normal individual with no renal or vascular disease. A higher level of cLDL and/or auto antibody to cLDL in test individual as compared to that normally present is indicative that this individual is at risk of atherosclerosis.

In another embodiment of the instant invention, a method is provided of assessing the effectiveness of a treatment for an atherosclerosis-related disease in an individual in need of such assessment, comprising the step of monitoring cLDL and/or antibody to cLDL in this individual. A decrease in the level of either cLDL or antibody to cLDL as compared to pretreatment levels is indicative that the treatment being tested is effective against atherosclerosis.

Yet another embodiment of the instant invention provides a method of reducing carbamylation in an individual in need of such treatment, comprising the step of treating said individual with enzymatic or non-enzymatic inhibitors of carbamylation.

In yet another embodiment is provided a method for reducing the level of cLDL in an individual by the direct removal of cLDL from blood or plasma. This method comprises using cLDL antibodies for ex vivo binding and removal of cLDL.

In yet another embodiment of the instant invention, a method of treating or preventing atherosclerosis in an individual in need of such inhibition, comprising the step of inhibiting aggregation and/or deposition of cLDL in said individual, is provided.

So that the matter in which the above-recited features, advantages and objects of the invention, as well as others, which will become clear, are attained and can be understood in detail, more particular descriptions of the invention are briefly summarized. The above may be better understood by reference to certain embodiments thereof, which are illustrated in the appended drawings. These drawings form a part of the specification. It is to be noted; however, that the appended drawings illustrate preferred embodiments of the invention and therefore are not to be considered limiting in their scope.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate embodiments of the invention and therefore are not to be considered limiting in their scope.

FIG. 8A shows cross-reactivity of cLDL antisera with nLDL and oxLDL and cross-reactivity of nLDL antisera with cLDL and oxLDL. FIG. 8B shows that cLDL and nLDL antibodies can be purified using affinity chromatography so as to lose all of its cross-reactivity.

FIG. 9A shows that when cLDL is added to PBS as little as 3 picogram of cLDL can be detected using this assay. FIG. 9B shows that as little as 30 picogram of cLDL can be detected in plasma.

FIG. 14 shows increase in blood plasma cLDL in hemodialysis patients with thickened carotid artery intima-media thickness (IMT). FIG. 14A shows this increase without any adjustment to the values obtained while FIG. 14B shows the values with adjustment to the concentration of total cholesterol and FIG. 14C with adjustment to the concentration of or nLDL. Data are shown as mean±SEM; n=18-23; *p=0.015-0.033.

DETAILED DESCRIPTION OF THE INVENTION

Figure 1:
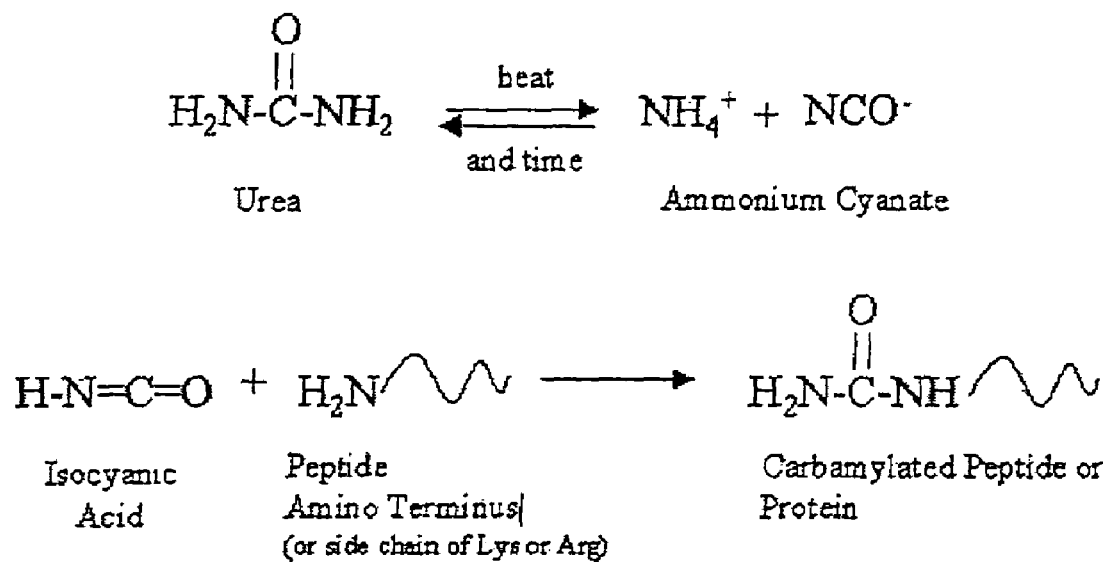
FIG. 1 shows an example of the carbamylation reaction of free amino groups of the N-terminal protein.

CLDL-cholesterol (cLDL), by virtue of its ability to cause endothelial cell damage, leads to accelerated atherosclerosis and contributes significantly to cardiovascular complications in patients with renal failure. An additional contributory factor is related to cLDL-cholesterol forming more aggregates than native LDL-cholesterol (nLDL), resulting in its deposition in the arterial wall. In addition, because urea is normally present in the blood of all humans, cLDL may also play an important role in atherosclerosis in individuals with normal kidney function.

The instant invention is directed to a method of determining whether an individual is at risk for atherosclerosis, comprising the step of measuring the level of carbamylated LDL and/or cLDL auto antibody in a sample obtained from the individual. Preferably, when the level of carbamylated LDL and/or cLDL auto antibody in the sample is greater than normal as established by standard laboratory methodology in subjects with no known vascular or renal disease, the individual is at risk for atherosclerosis. Generally, the sample is selected from the group consisting of plasma and urine. The level of carbamylated LDL in the sample is determined using an antibody to carbamylated LDL, autoimmune antibody to carbamylated LDL, or any other method known to a person having ordinary skill in this art.

The instant invention is directed to a method of assessing the effectiveness of a prevention and treatment for an atherosclerosis-related disease in an individual in need of such assessment, comprising the step of monitoring carbamylated LDL and/or antibody to carbamylated LDL in the sample. If there is a decrease in the levels of cLDL and/or antibody to carbamylated LDL as compared to pretreatment levels then the treatment can be considered effective.

The present invention describes that carbamylated LDL causes endothelial dysfunction and other effects that are linked to atherosclerosis, and therefore, a central premise of the present invention centers on a reduction of carbamylated LDL by any means as a beneficial treatment. Accordingly, the present invention is further directed to a method of treating an individual having an undesirably high level of carbamylated LDL by reducing or inhibiting further carbamylation of LDL or reducing the existing cLDL level in the individual. In this aspect treating the individual with enzymatic or nonenzymatic inhibitors of carbamylation can inhibit the carbamylation of cLDL. Using agents that can sequester cLDL such that cLDL is naturally eliminated from the body can on the other hand reduce the level of cLDL.

The present invention is also directed to a method of reducing carbamylation in an individual in need of such reducing treatment, comprising the step of treating the individual with a monomeric amino acid. Representative examples of useful monomeric amino acids include lysine, glycine, and arginine.

Preferably, the amino acid is administered in a dose of from about 5 mg/kg to about 500 mg/kg. In one aspect, this method is useful for treating an individual susceptible to atherosclerosis. In another aspect, this method is useful for treating an individual with renal disease such as an individual with advanced renal failure requiring dialysis and/or transplantation. In yet another aspect this method may be used to reduce carbamylation in an individual with normal renal function.

The present invention is further directed to a method of treating an individual having an undesirably high level of CLDL, comprising direct removal of cLDL from blood or plasma. The blood or plasma to be treated is passed through a dialyzer containing immobilized cLDL antibodies. The antibodies bind and retain cLDL and treated blood or plasma is returned back to the individual. In this embodiment, the individuals that may benefit from such treatment are as described supra. Generally the cLDL antibodies may be immobilized on the dialyzing membrane or may be immobilized on agarose or other such biocompatible particles, which are then packed in a column within the dialyzer. In one aspect, the removal of cLDL can be combined with hemodialysis or with plasmophoresis.

The following terms are described herein to clarify the subject matter disclosed in the instant specification:

'Hemodialyis' is the use of a machine to clean wastes from the blood. The blood travels through a dialyzer, which removes wastes and extra fluid the cleaned blood is then returned back to the body. Hemodialysis is often employed in individuals with impaired kidney function.

'Plasmophoresis' is a procedure in which blood is mechanically taken out of the body and separated into red blood cells and plasma. The plasma is discarded and replaced with a fresh solution of plasma substitute or/and albumin. This method is generally employed to remove excess antibodies from plasma, especially to suppress undesirable immune response.

'Aphereis' is a procedure where whole blood is removed from the body and a desired component is retained while the remainder of the blood is returned to the donor. The desired component may be cleared from the blood using any method such as dialysis or affinity binding of the component by a ligand such as an antibody.

The present invention is also directed to a method of treating or preventing atherosclerosis in an individual in need of such inhibition, comprising the step of inhibiting aggregation and/or deposition of carbamylated LDL in the individual. Such inhibition prevents cell damage caused by carbamylation of LDL in the individual, such as endothelial cell and/or vascular smooth muscle cell damage, or the adhesion of monocytes.

The present invention is also directed to an antibody directed against cLDL. Such an antibody could be either monoclonal or polyclonal. The present invention is also directed to a kit comprising the antibody of the present invention. Preferably, the biological sample that is tested with this kit is blood or plasma sample. The container means of the kits will generally include at least one vial, test tube, flask, bottle, or even syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits of the present invention will also typically include a means for containing the antibody, antigen, and any other reagent containers in close confinement for commercial sale. Such containers may include injection or blow-molded plastic containers into which the desired vials are retained.

The following examples are given for the purpose of illustrating various embodiments of the invention and are not meant to limit the present invention in any fashion.

EXAMPLE 1

Cell Culture

Human coronary artery endothelial cells (HCAECs) and vascular smooth muscle cells (VSMCs) were obtained from Clonetics, (Walkersville, Md.). Human coronary artery endothelial cells were maintained in EGM-2-MV medium (Clonetics) and vascular smooth muscle cells were maintained in SmBM medium (Clonetics), both supplemented with 5% fetal bovine serum, growth factors, and antibiotics (gentamycin, amphotericin B). Cells were grown in a humidified incubator (5% $CO_2$, 37° C.), and culture medium was changed every other day. In all experiments, human coronary artery endothelial cells and vascular smooth muscle cells were used at passages between 4 and 7.

EXAMPLE 2

Human Native LDL

Human native LDL (nLDL) was purchased from Fluka (Milwaukee, Wis.) and stored at +4° C. in nitrogen atmosphere to prevent oxidation.

EXAMPLE 3

CLDL

CLDL (cLDL) was produced by chemical modification of nLDL. Native LDL was incubated under sterile conditions with potassium cyanate (Aldrich; Milwaukee, Wis.) (20 mg KOCN/mg nLDL) at 35° C. for 4 hours. Salt was removed by excessive dialysis against 0.15 M NaCl, 0.01% EDTA, pH 7.0 at 4° C. for 48 hours under sterile conditions. To obtain cLDL carbamylated to different degrees, various incubation periods, from 5 to 300 min, were used.

EXAMPLE 4

Oxidized LDL

Oxidized LDL (oxLDL) was obtained by incubation of nLDL at 1.5 mg/ml concentration with freshly prepared sterile 5 μM CuSO$_4$ for 24 hours at 37° C., after removal of EDTA by dialysis in sterile conditions against phosphate-buffered saline (PBS), pH 7.4 for 24 hours at 4° C. The reaction was stopped by adding 200 μM sterile EDTA.

EXAMPLE 5

Carbamylated-oxidized LDL

Carbamylated-oxidized LDL (coxLDL) was obtained by oxidation of cLDL. All modified LDL forms were kept at 4° C. away from light, and used within 2 weeks after preparation.

EXAMPLE 6

Protein Concentration

Protein concentration was measured by the BCA protein assay (Pierce; Rockford, Ill.).

EXAMPLE 7

Electrophoresis of LDL Isoforms

Electrophoresis of LDL isoforms was carried out in 0.5% agarose gel in barbital buffer, pH 8.6 for 1 hour (7 μg LDL protein/well, 90 V, 70 mA), and the bands were stained in Sudan Black B.

EXAMPLE 8

Assessment of Carbamylation

Assessment of carbamylation was made (a) on the basis of relative electrophoretic mobility in agarose gel, and (b) by the homocitrulline assay as described by Trepanier et al. [10]. Briefly, 25 μg of LDL protein in PBS, pH 7.4 (50 μl volume) was incubated with 2 μg proteinase K and 1% SDS (v:v) at 37° C. for 2 hours. Then 250 μl of urea-nitrogen reagent (0.83 M sulfuric acid, 1.13 M orthophosphoric acid, 0.55 mM thiosemicarbazide, 2.6 mM cadmium sulfate), 50 μl 3% diacetyl monoxime in water was added and the mixture was incubated at 97° C. for 30 min. Samples were transferred into a 96-well plate and absorption of chromogen(s) was recorded at 530 nm. Homocitrulline (carbamyl lysine) standard curves (0-30 nmol) were generated using serial dilutions of a stock solution (200 μM) in PBS, pH 7.4. Results are expressed as nmol homocitrulline/mg LDL protein).

EXAMPLE 9

Assessment of Oxidation

Assessments of oxidation were made (a) on the basis of relative electrophoretic mobility in agarose gel, and (b) using a thiobarbituric acid reactive substances (TBARS) assay [11]. LDL protein (25 μg in 50 μl PBS) was mixed with 150 μl of freshly prepared 0.67% thiobarbituric acid, 20% trichloroacetic acid and heated at 95° C. for 45 min. Butylated hydroxytoluene (20 μM) and EDTA (100 μM) were added to prevent further oxidation during heating. After cooling the samples to room temperature, 300 μl butanol was added for extraction, and the samples were centrifuged at 4000 rpm for 10 min. The supernatant (200 μL) was transferred into a 96-well plate, and assayed spectrophotometrically at 532 nm in a plate reader. Freshly prepared 1,1,3,3-tetramethoxypropane, which yields malondialdehyde (MDA), was used as a standard. The results are expressed as nmol MDA/mg LDL protein.

EXAMPLE 10

Cell Viability

Cell viability was determined by trypan blue exclusion and LDH release as previously described [12]. For the LDH release measurements, the LDH release assay (Promega; Madison, Wis.) was used. Apoptosis was measured using nuclear staining as described and by annexin V/propidium iodide staining. For Annexin V and propidium iodide staining, human coronary artery endothelial cells were cultured (2×10$^5$ cells per well in 6 well plates) in 5% FBS supplemented medium overnight and then treated with LDL. The supernatant and cells obtained with trypsin/EDTA were centrifuged at 1000 rpm for 5 min; cells were combined and washed in PBS, pH 7.4, centrifuged, and resuspended in 200 μl binding buffer. Annexin V (Clontech; Palo Alto, Calif.) (5 μl) and propidium iodide (Clontech) (10 μl) were added and incubated at room temperature in the dark for 15 min. After 300 μl binding buffer was added, FACS analysis was immediately performed using a flow cytometer/cell sorter (Becton Dickinson, Mountain View, Calif.). The percentage of apoptotic cells was calculated by the CELLQUEST software package. Cell viability and proliferation were measured using an MTS assay (CellTiter 96 Aqueous One Solution Cell Proliferation assay kit, Promega Corporation, Madison, Wis.), or a bromodeoxyuridine assay (BrdU cell proliferation assay kit, Oncogene, Cambridge, Mass.). For Western blot analysis, protein samples were resolved by agarose gel electrophoresis as described above. Proteins were electrophoretically transferred to nitrocellulose or to immobilon polyvinylidine difluoride (Millipore, Bedford, Mass.) membranes, and reacted with antibody as described by Towbin [13]. A statistical comparison of the data was carried out using the Student's t-test, and $p<0.05$ was considered to be significant.

EXAMPLE 11

In Vitro Carbamylation and Oxidation of LDL

Figure 2:
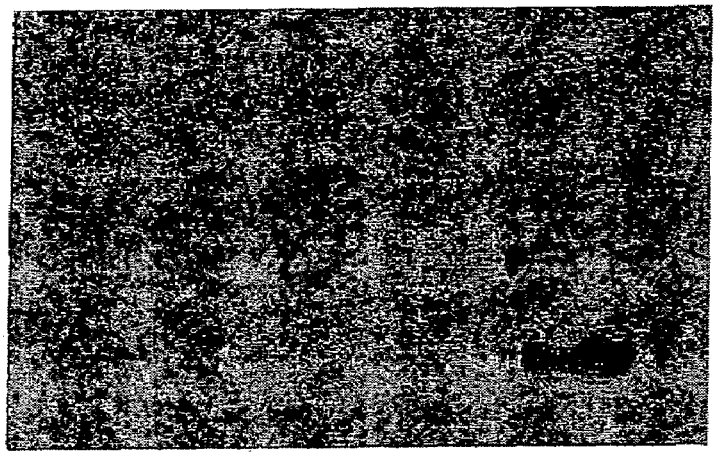
FIG. 2 shows that after human LDL was carbamylated in vitro in the presence of potassium cyanate (20 mg/mg LDL protein), or oxidized by exposure to 5 μM cupric sulfate, the isoforms have different mobility in agarose gel.

Human LDL was carbamylated in vitro in the presence of potassium cyanate (20 mg/mg LDL protein), or oxidized by exposure to 5 μM cupric sulfate as described above. The isoforms have different mobility in agarose gel (FIG. 2).

EXAMPLE 12

Human LDL-cholesterol can be Carbamylated In Vitro to Different Decrees

Figure 3:
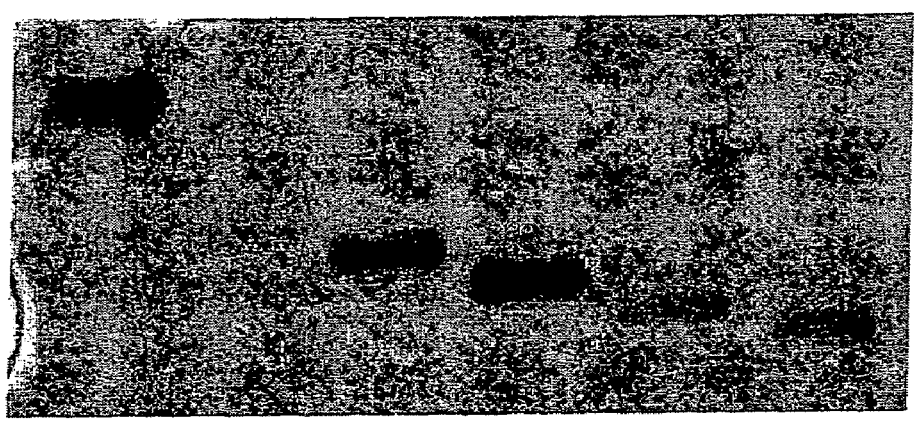
FIG. 3 shows that exposure of human normal LDL to potassium cyanate (20 mg/mg LDL protein) for 15 to 240 minutes led to gradually increased mobility of the cLDL in agarose gel.

Since the level of LDL carbamylation in humans is not known, it is necessary to have methods to study LDL carbamylated to different degrees. Exposure of human normal LDL to potassium cyanate (20 mg/mg LDL protein) for 15 to 240 min led to gradually increased mobility of the cLDL in agarose gel (FIG. 3). The degree of carbamylation measured using a homocitrillune assay was gradually increased from 94±14 nmol homocitrulline/mg LDL protein after 15 min to 221±32 nmol homocitrulline/mg LDL protein after 240 min of carbamylation.

EXAMPLE 13

CLDL Induces Injury to Endothelial Cells In Vitro

Figure 4:
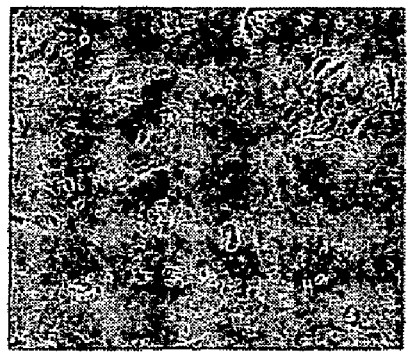
FIG. 4 shows that endothelial cell morphology is changed after treatment with carbamylated LDL. Cells treated with 200 μg/ml cLDL showed morphological signs of deterioration as compared to cells treated with the same amount of native LDL. The cells look damaged, they are smaller than normal and shrunken, and some of them are detached from the plastic surface. The monolayer is disrupted. Spaces between cells are filled with cellular debris.
Figure 4:
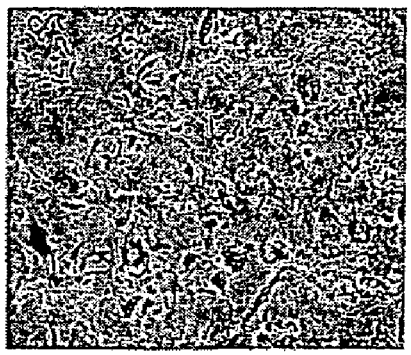
Figure 4:
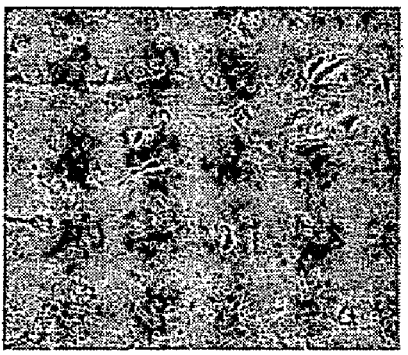
Figure 4:
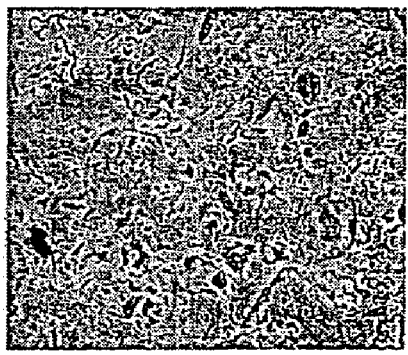

Cultured human coronary artery endothelial cells treated with 50-400 μg/ml cLDL for 24 hours showed, under light microscopy, signs of morphological alterations, detachment and presence of cellular debris (FIG. 4). The cells look smaller (shrunken), which is indicative of apoptosis.

EXAMPLE 14

CLDL Induces Irreversible Cell Injury

Figure 5:
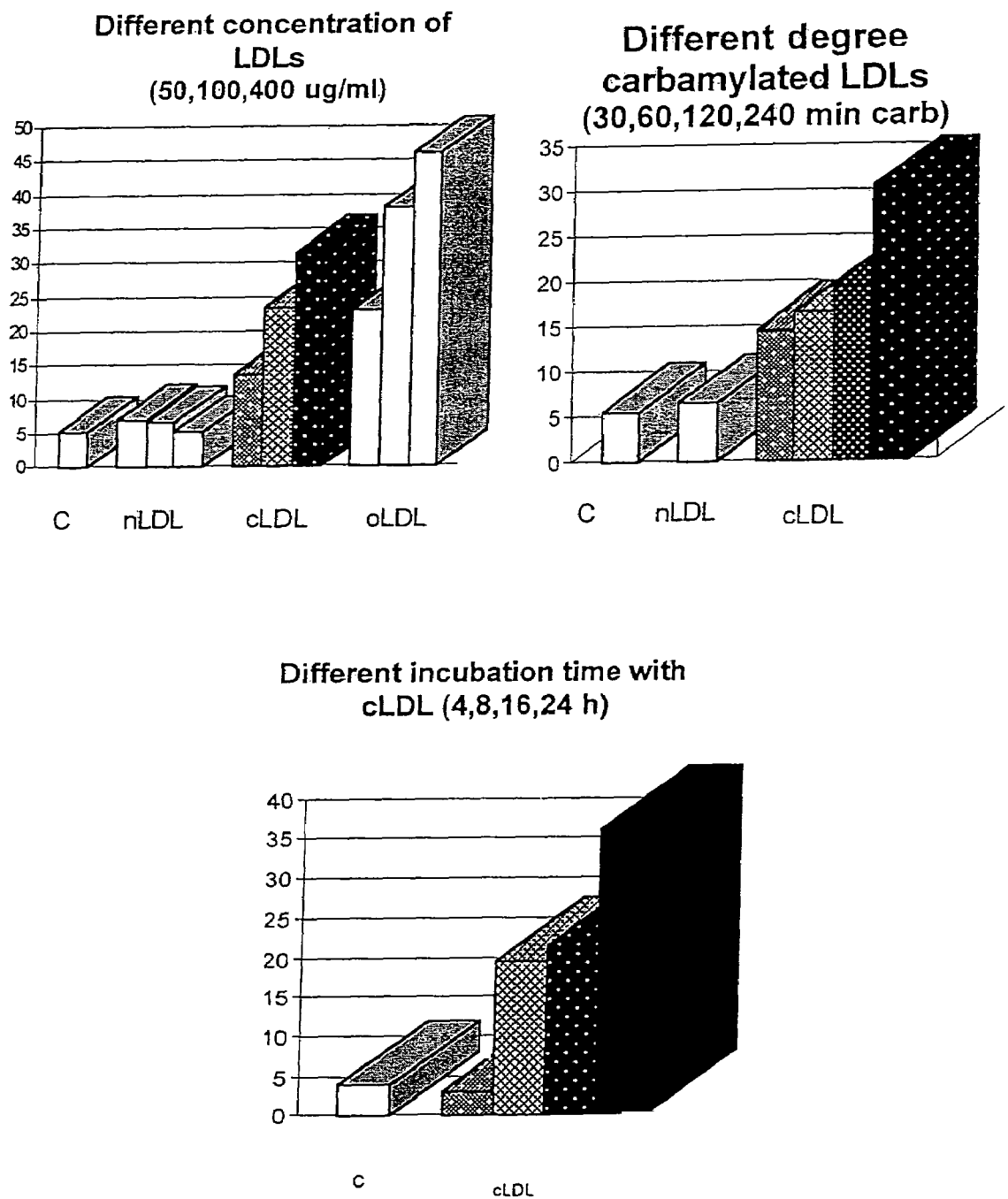
FIG. 5 shows LDH release by cultured human endothelial cells treated with native (nLDL), carbamylated (cLDL), or oxidized LDL (oLDL).

CLDL induces irreversible cell injury as measured by LDH release (FIG. 5). This injury was dose- and time-dependent, and correlated with the degree of LDL carbamylation (between 90 and 220 nmol homocitrulline/mg protein). At 200 μg/ml cLDL, the LDH release was 21.3±4.6% compared to 6.6 ±3.2% (n=5) induced by native LDL.

EXAMPLE 15

At Least Part of the Cellular Population Dies by Apoptosis

Figure 6:
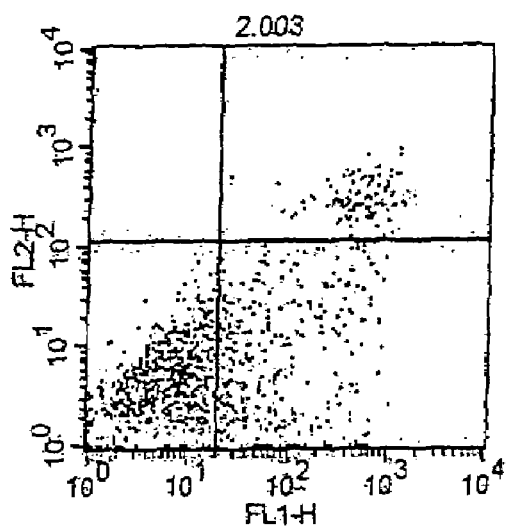
FIG. 6 shows that cLDL induces apoptosis of human coronary endothelial cells. FACS analysis of endothelial cells stained with propidium iodide/Annexin V after being treated with 200 μg/ml nLDL or 200 μg/ml cLDL for 24 hours. More cells are visible in the lower right quadrant of the plot (annexin V staining).
Figure 6:
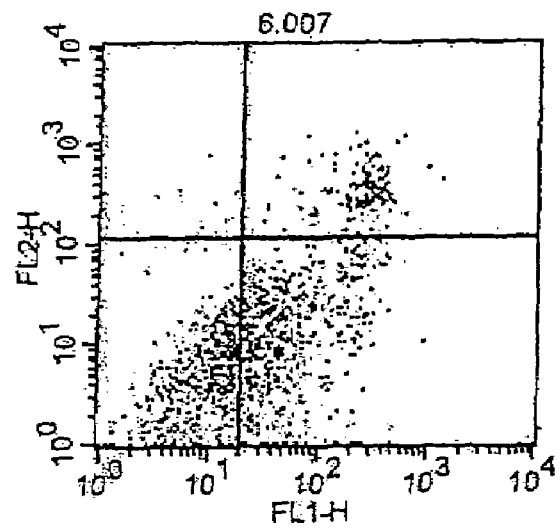

Flow cytometry using Annexin V staining also demonstrated the presence of apoptotic cell death (FIG. 6). The portion of Annexin V-positive cells was 11±2% in non-treated cells, 14±3% in nLDL treated, and 24±4% in cLDL treated cells (200 μg/ml LDL for all isoforms). The cytotoxicity of cLDL was less than that induced by oxLDL in parallel experiments (data not shown).

EXAMPLE 16

In Vitro Carbamylation of LDL can be Inhibited with Monomeric Amino Acids

Figure 7:
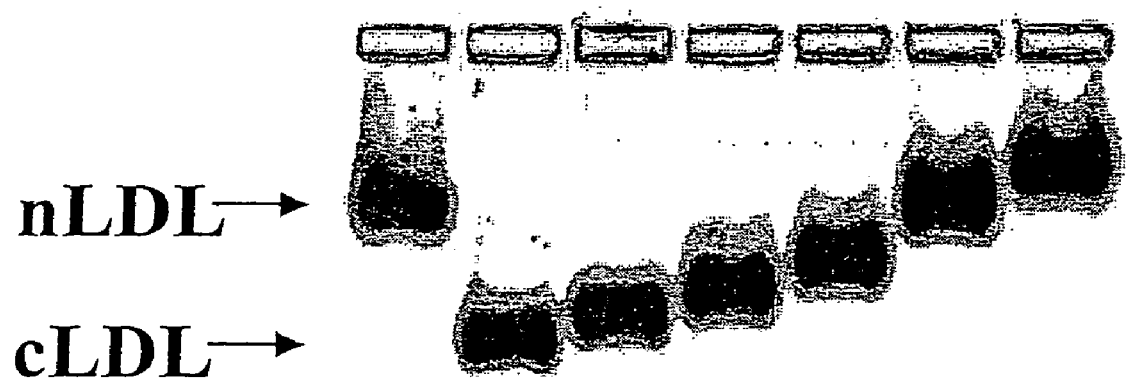
FIG. 7 shows in vitro inhibition of LDL carbamylation with L-lysine.

Monomeric amino acids (L-lysine, L-arginine, L-glycine) can inhibit carbamylation of LDL in vitro when applied in molar ratios of 1:1 to 16:1 (L-lysine:KOCN) (FIG. 7).

EXAMPLE 17

Amylation has Little or No Effect on Oxidation of LDL In Vitro, and Vice Versa

Gradually cLDL (90 to 220 nmol homocitrulline/mg protein) was oxidized in vitro and the level of oxidation examined using a thiobarbituric acid reactive substances (TBARS) assay. These results showed that susceptibility of LDL to oxidation was in the range of 60-70 nmol malonaldehyde/mg protein, which was not increased after carbamylation. Instead, some competitive inhibition (up to 20%) between carbamylation and oxidation of lysine residues was observed. Another experiment, in which the LDL was gradually oxidized in vitro and tested for carbamylation, demonstrated no effect of oxidation on carbamylation of the same substrate (data not shown).

EXAMPLE 18

As Opposed to Native LDL, cLDL is More Likely to Form Aggregates and Precipitate from Solutions The aggregation in LDL isoforms' solutions was measured using ultrafiltration through 0.22 μm filter or ultracentrifugation at 14,000 g for 10 min. The results presented in Table 1 show that cLDL's ability to form aggregates is higher than that of nLDL. Aggregation of cLDL may contribute to atherosclerotic plaque formation.

TABLE 1

Aggregation of LDL isoforms in solution
(% lost during centrifugation or ultrafiltration)

| LDL isoform | Centrifugation | Filtration |
| --- | --- | --- |
| nLDL | 10 | 38 |
| cLDL | 26 | 62 |

EXAMPLE 19

Antibody to cLDL

Figure 8A:
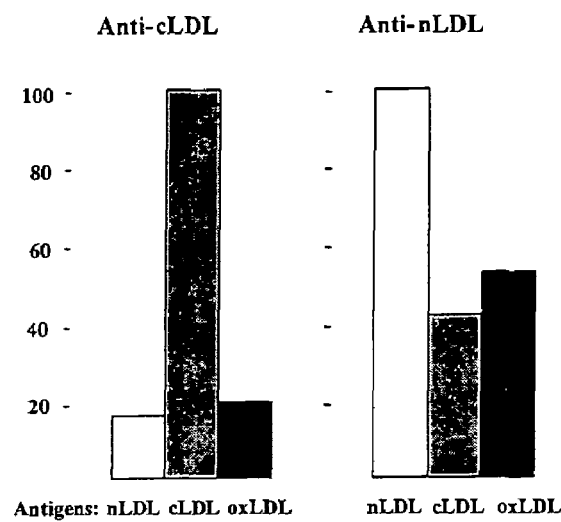
FIGS. 8A-8B show reactivity of rabbit antisera raised to LDL isoforms.
Figure 8B:
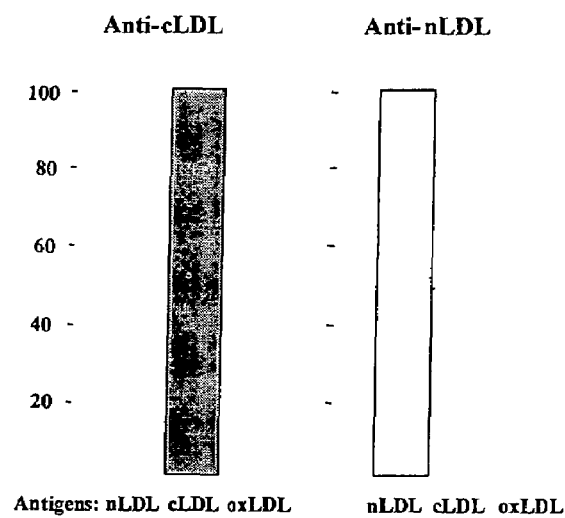
Figure 9B:
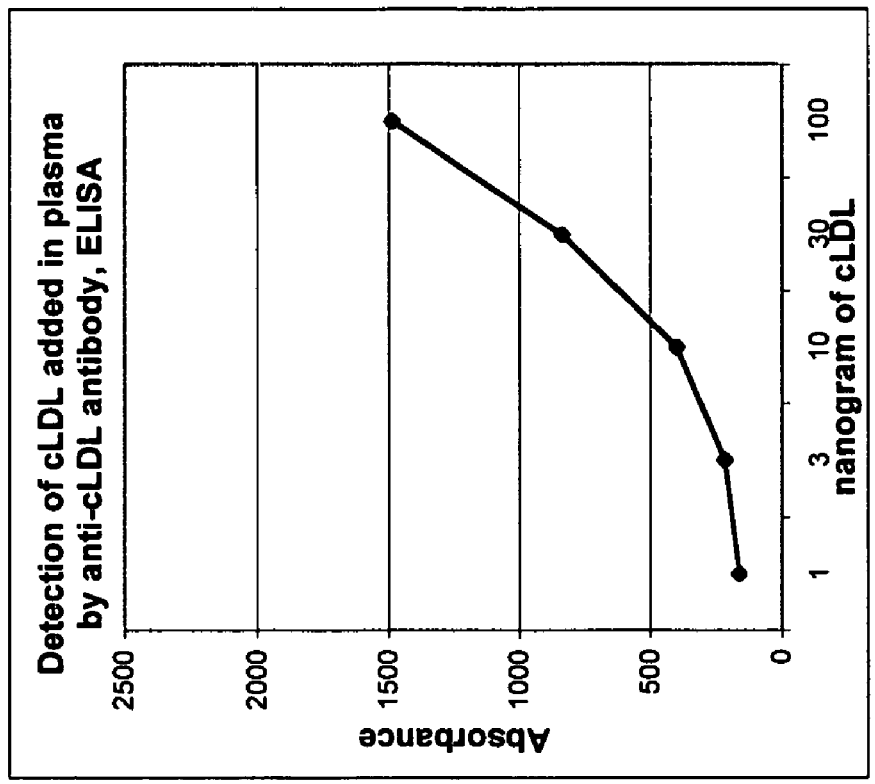
FIGS. 9A-9B show the sensitivity of ELISA for detecting cLDL using cLDL antibody.
Figure 9A:
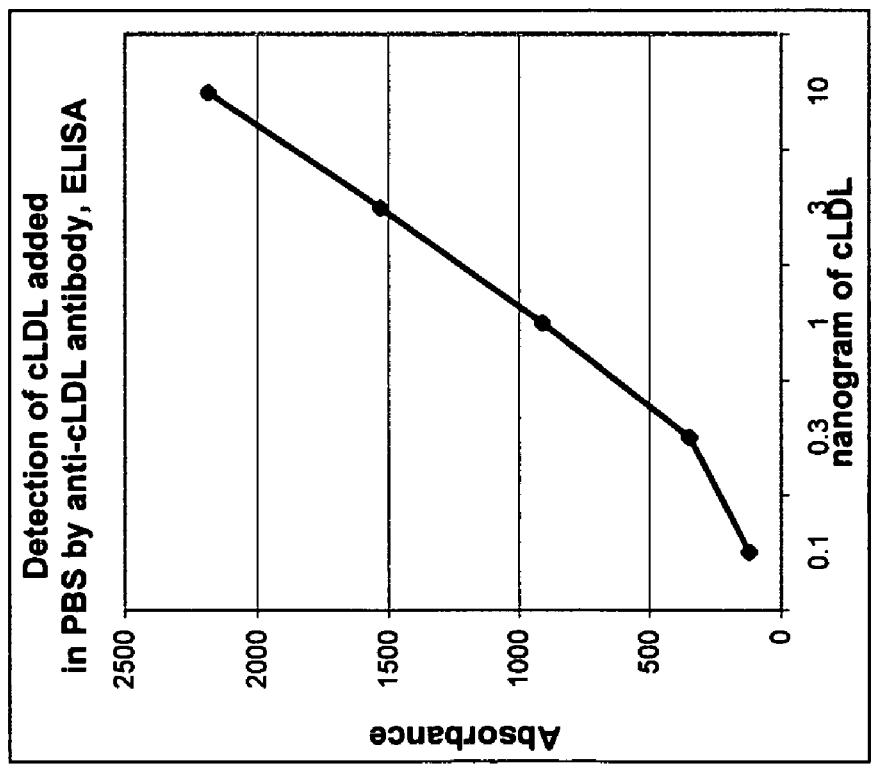

Antibody to cLDL is not commercially available. In vitro modified cLDL and oxLDL, as well as nLDL, were used for raising polyclonal antibody in rabbits. Although the obtained antisera analyzed by quantitative Western blotting have some cross-reactivity, both anti-cLDL and anti-nLDL were more specific to their direct antigens (FIGS. 8A-8B). These antibodies can be purified using affinity (immunosorption) chromatography so as to lose most or all of the cross-reactivity. The antibodies were sensitive enough to detect as little as 30 pg of LDL protein in plasma using an ELISA assay (FIGS. 9A-9B). Antisera to oxLDL did not have any specificity (data not shown) and was excluded from the studies. If necessary, commercial monoclonal antibody to human oxLDL (Research Diagnostics, Flanders, N.J.) may be used.

EXAMPLE 20

Protein Carbamylation is Increased in Patients with End-stage Kidney Disease (ESRD)

Figure 10:
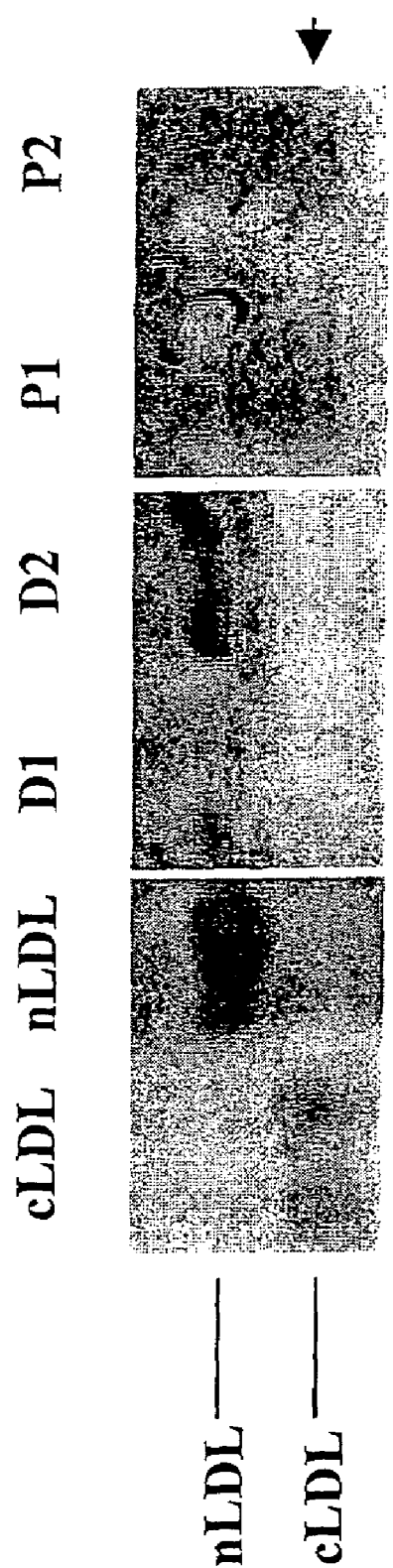
FIG. 10 shows the identification of carbamylated LDL in patients with end stage renal disease using Western blotting of human plasma proteins with anti-cLDL. Patients (P1 & P2) but not donors (D1&D2) have a second band (shown by arrow) which reacts with anti-cLDL and has the mobility of cLDL in agarose gel.
Figure 11:
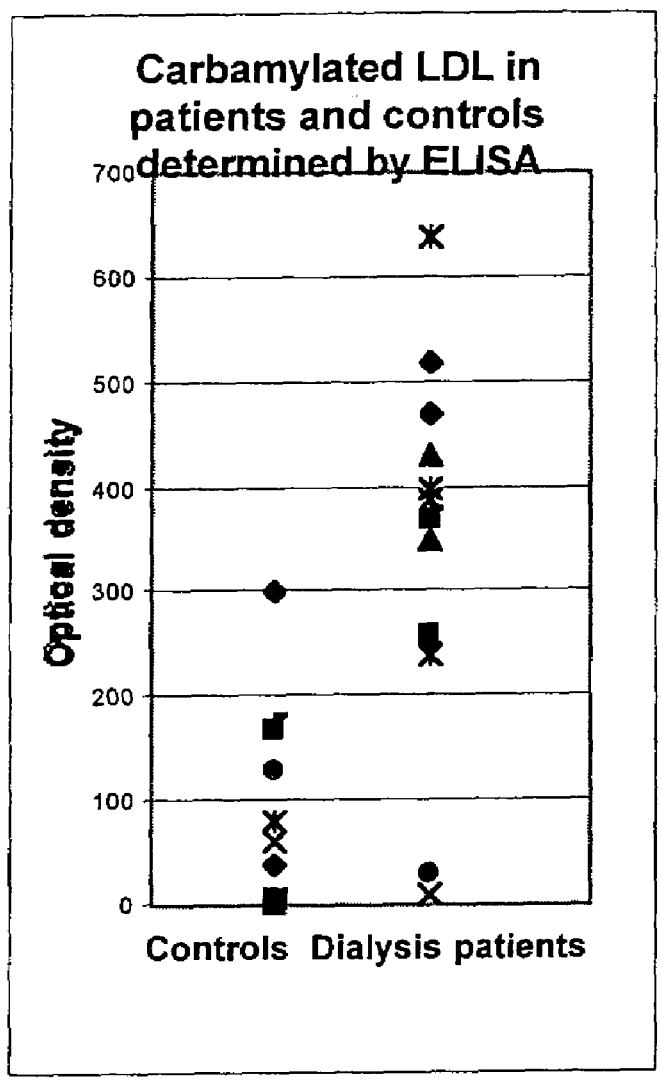
FIG. 11 shows cLDL in end stage renal disease patients and controls determined by using specific anti-cLDL antibodies. Results are presented as absorbance at 450 nm.

Although the presence of carbamylated proteins has been reported in patients with renal failure, the presence of cLDL in plasma has not been previously examined. In order to produce a tool for studying cLDL, cLDL was prepared and polyclonal antibodies to cLDL and nLDL was raised in rabbits as described above. In pilot experiments, plasma from patients with end-stage kidney disease was subjected to electrophoresis in agarose and subsequent immunoblotting with anti-cLDL antibody to detect the presence of modified LDL. The high mobility in agarose (due to increased charge of the molecule as compared to nLDL) corresponding to cLDL, as well as interaction with anti-cLDL antibody, indicates that the modified LDL is cLDL (FIGS. 9, 10). The plasma from the same patients demonstrated increased total levels of carbamylation of lysine residues in proteins (43±6 versus 14±3 nmol homocitrulline/mg protein in donors). The ELISA assay showed a significant increase of cLDL in dialysis patients (absorption: 0.340±0.045, n=15) versus healthy individuals (0.104±0.032, n=9, p<0.01) (FIG. 11). This increase correlated with the elevation of the total carbamylation of proteins in plasma (43±6 vs. 14±3 nmol homocitrulline/mg protein in healthy subjects). A more quantitative assay to measure an antigen, competitive ELISA, also showed that cLDL content in patients is increased (0.350±0.030, n=15, vs. 0.270±0.020, n=15, in healthy individuals, p<0.03).

EXAMPLE 21

Elevation of Autoantibody to cLDL in Dialysis Patients

Figure 12:
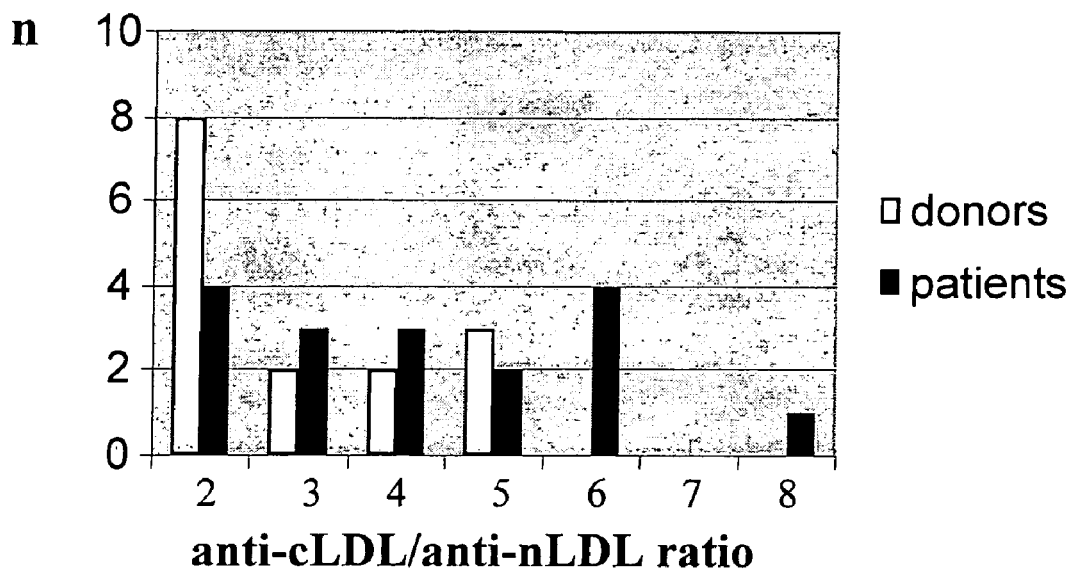
FIG. 12 shows increased anti-cLDL autoantibody (anti-cLDL/anti-nLDL ratio) in end stage renal disease patients.

CLDL is highly immunogenic when used as an antigen in rabbits. Both hemodialysis patients and healthy individuals have autoantibodies to cLDL. Increased anti-cLDL antibody was detected (anti-cLDL/anti-nLDL ratio) in patients with chronic renal failure (FIG. 12). Also, in these patients autoantibody to cLDL are mainly against moderately cLDL, rather than mildly or heavily cLDLs. Taken together, these data suggest that both elevated cLDL and autoantibody to cLDL are potential pathogenic factors in the development of atherosclerosis in renal patients.

EXAMPLE 22

Association Between Common Carotid Artery Intima-media Thickness (CCA-IMT) and cLDL Common carotid artery intima-media thickness (CCA-IMT) is a commonly used quantifiable marker of early atherosclerosis. Median population values of common carotid artery intima-media thickness range between 0.4 and 1.0 mm, while measurements greater than or equal to 1.0 mm are generally accepted as abnormal [17]. The value of common carotid artery intima-media thickness and plasma level of cLDL was evaluated in hemodialysis patients to evaluate a potential link between elevated levels of cLDL and atherosclerosis in these patients.

Fasting serum samples collected before dialysis were used for the measurements of cLDL and native LDL (nLDL). Sandwich ELISA was performed according to a known procedure [18]. The common carotid artery intima-media thickness was measured by B-mode ultrasonography using a high-resolution ultrasound unit (ATL HDI 5000 Philips, Bothell, Wash., USA) equipped with a 5-to-12 MHz linear transducer in patients who had been on chronic hemodialysis for a mean of 43±31 months. The patients were scanned in the supine position with the neck extended and the head turned away from the carotid artery being scanned. Longitudinal images were obtained from the far wall of the most distal segment of the common carotid artery defined as the one-cm segment just proximal to the beginning of the dilatation of the carotid bulb, with loss of the parallel configuration of the near and far walls of the common carotid artery. Arterial wall intima-media thickness was defined as the total thickness of the inner echogenic line and inner hypoechoic layer of the visualized arterial wall. The thickest intima-media thickness value was acquired at the defined common carotid artery segment excluding sclerotic or nonsclerotic atheromateous plaques. The mean of the right and left common carotid artery intima-media thickness values was accepted as the common carotid artery intima-media thickness value of each patient.

Figures 14A, 14B, 14C:
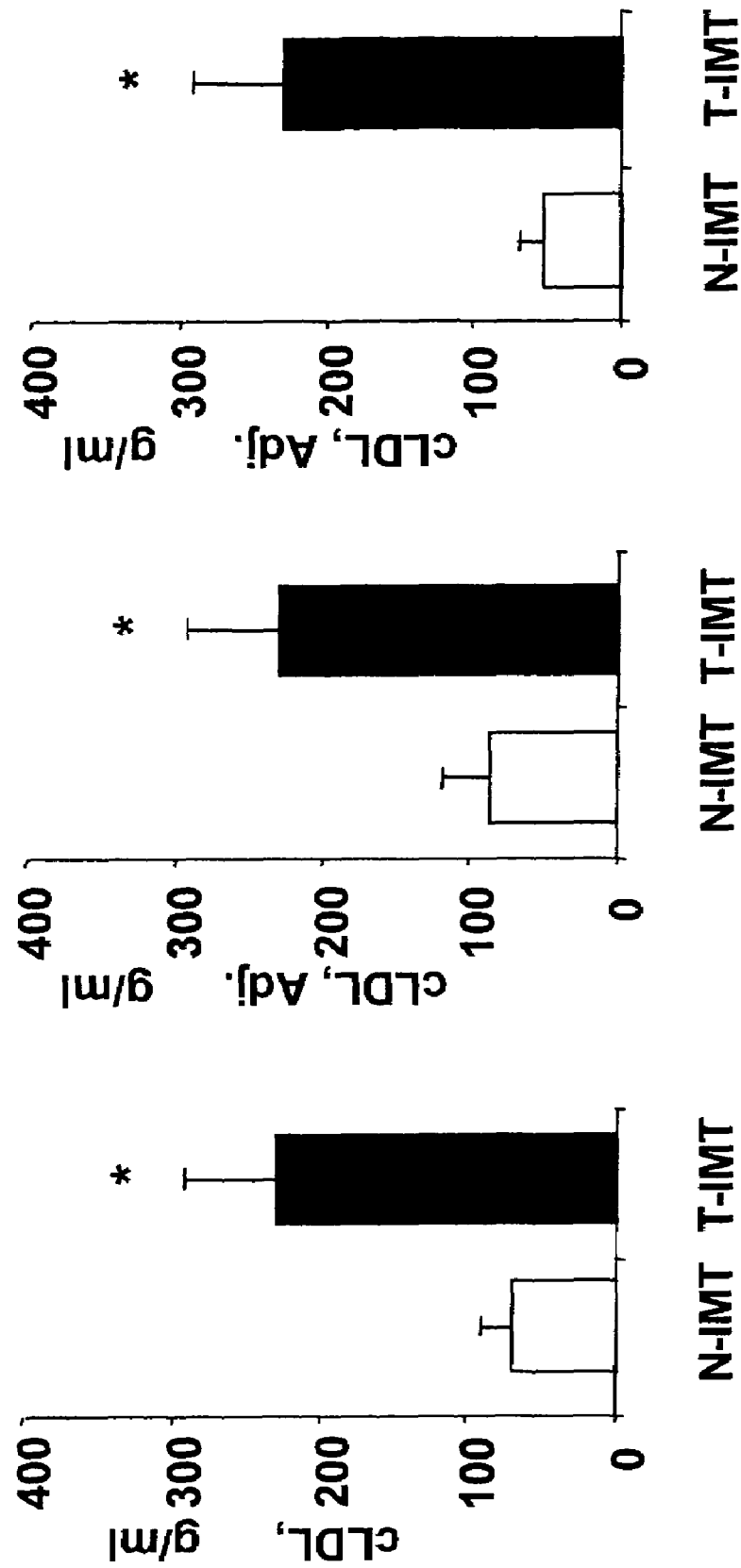

The patients were divided into two groups based on the IMT. The normal IMT (N-IMT) and thick IMT (T-IMT) groups were matched by age and sex, and had no significant difference by all used criteria (except the blood pressure) (Table 2). FIG. 14A shows that cLDL levels are significantly increased in thick intima-media thickness patients (230.5±58.2 µg/ml vs. 71.9±18.5 µg/ml in N-intima-media thickness patients, p=0.015). Because carbamylation is a non-enzymatic process, it may depend on the concentration of the total cholesterol. FIG. 14B shows that cLDL concentrations were significantly different between the two groups of patients even after adjustment for total cholesterol (230.5±58.2 µg/ml in thick intima-media thickness patients, and 86.4±27.2 µg/ml in normal-intima-media thickness patients, p=0.033) (FIG. 1B), or for the concentration of nLDL measured by sandwich ELISA (230.5±58.2 µg/ml in T-intima-media thickness group vs. 50.5±12.6 µg/ml in normal-intima-media thickness patients, p=0.017) (FIG. 1C). As T-intima-media thickness is a positive marker for atherosclerosis, the high level of cLDL in patients with T-intima-media thickness demonstrates a potential link between carbamylation of LDL and atherosclerosis in hemodialysis patients.

TABLE 2

Characterization of patients into N-IMT and T-IMT groups

| PARAMETER* | N-IMT (n = 18) | T-IMT (n = 23) | pt value |
|---|---|---|---|
| IMT, mm | 0.60 ± 0.02 | 1.10 ± 0.02 | <0.0001 |
| Age, years | 53.6 ± 2.5 | 59.6 ± 1.8 | n/s |
| Sex | 1.5 | 1.4 | n/s |
| Body weight, kg | 60.0 ± 2.2 | 58.6 ± 1.8 | n/s |
| Cardiothoracic index | 0.48 ± 0.01 | 0.47 ± 0.01 | n/s |
| Systolic BP, mm Hg | 110 ± 3 | 124 ± 5 | 0.014 |
| Diastolic BP, mm Hg | 67 ± 2 | 73 ± 2 | 0.025 |
| Albumin, g/dl | 3.9 ± 0.1 | 3.6 ± 0.1 | n/s |
| Total cholesterol, mg/dl | 174.7 ± 7.4 | 190.3 ± 11.3 | n/s |
| Triglycerides, mg/dl | 168.6 ± 17.3 | 197.8 ± 25.4 | n/s |
| BUN, mg/dl | 62.2 ± 2.7 | 65.9 ± 3.3 | n/s |

EXAMPLE 23

Removal of cLDL by Apheresis

LDL apheresis has been used to remove LDL from blood or plasma in patients with high levels of LDL such as in hypercholesterolemia (19,20,21,22). In this method, the antibody to LDL is covalently bound to a dialysis membrane or agarose particles. Blood or plasma to be treated is passed through a dialyzer column filled with immobilized LDL during hemodialysis or plasmophoresis, respectively. The LDL particles bind to the LDL antibody and thus blood is cleared of excess LDL. Four different systems currently used for LDL apheresis are LIPOSORBER (Kaneka, Osaka, Japan), THERA-SORB (Baxter, Munich, Germany), LIPOPAK (Pocard, Moscow, Russia) and DALI (Fresenius, St. Wendel, Germany). Average reductions of 50.6% for total cholesterol, 52.2% for LDL, 64.3% for Lp(a) and 43.1% for triglycerides has been achieved so far (23). By replacing LDL antibodies with cLDL antibodies, cLDL-apheresis can be used to directly remove cLDL from blood or plasma in individuals in need of such treatment. This will be especially beneficial in individuals with an abnormally high level of cLDL as the instant application shows a correlation between cLDL and atherosclerosis.

EXAMPLE 24

In Addition to Cell Death, cLDL Induces Proliferation of Endothelial Cells

The results of the MTS assay showed significant decreases in the numbers of cells treated with oxLDL and coxLDL, especially at high concentrations (at 200 µg/mL concentration, viability was 12±2% and 4±2%, respectively) (Table 2). On the other hand, the decrease was not seen in the number of cells treated with cLDL despite the presence of high LDH release assay results and assessment of cell injury/death under light microscopy (viability 118% for both nLDL and cLDL).

The results of the bromodeoxyuridine (BrdU) cell proliferation assay showed that cLDL causes a striking proliferation in human coronary artery endothelial cells (at 200 µg/mL, 298% with cLDL, vs. 92% with nLDL). The proliferative effect gradually increased with concentration of cLDL: percentage increases of 121, 209, 298, and 316% were seen with cLDL concentrations of 50, 100, 200, and 400 µg/ml, respectively. While oxLDL did not have a significant proliferative effect at similar concentrations, coxLDL showed a 227% proliferation increase compared to controls, besides a toxic effect similar to or greater than that of oxLDL (Table 3).

TABLE 3

The viability of cells treated with modified LDLs determined by MTS assay.

| | MTS assay Viability | | | |
|---|---|---|---|---|
| | 50 µg/mL | 100 µg/mL | 200 µg/mL | 400 µg/mL |
| Control | 97 ± 2 | | | |
| NLDL | 110 ± 9 | 118 ± 7 | 118 ± 8 | 136 ± 12 |
| CLDL | 102 ± 6 | 115 ± 6 | 118 ± 7 | 143 ± 14 |
| OxLDL | 72 ± 9 | 25 ± 9 | 12 ± 2 | 1.3 ± 0.4 |
| CoxLDL | 71 ± 9 | 21 ± 11 | 4 ± 2 | 0.7 ± 0.5 |

TABLE 4

The proliferation rate of cells treated with modified LDLs

| | BrdU cell proliferation assay Proliferation (%) | | | |
|---|---|---|---|---|
| | 25 µg/mL | 50 µg/mL | 100 µg/mL | 200 µg/mL |
| Control | 75 | | | |
| NLDL | 95 | 97 | 91 | 96 |
| CLDL | 112 | 121 | 209 | 298 |
| OxLDL | 107 | 107 | 106 | 165 |
| CoxLDL | 65 | 107 | 135 | 227 |

EXAMPLE 25

CLDL Induces both DNA Repair and DNA Synthesis in Endothelial Cells.

Flow cytometry of LDL-treated cells double-labeled with BrdU and 7-AAD (marker of total DNA) was performed to detect whether BrdU incorporation is linked to DNA synthesis or DNA repair, and whether mitosis is suppressed, and thus accumulation of polyploid cells is associated with the increase of BrdU incorporation. The data indicated that nLDL induces mainly DNA repair synthesis leading to increased BrdU incorporation in G0/G1 phase without any significant change in cell cycle. In contrast cLDL induces both DNA repair and DNA synthesis (17.0±1.1% vs. 8.3±0.7% and 7.2±1.4% cells in S-phase in nLDL-treated and non-treated cells, respectively). No accumulation of polyploid cells after cLDL or nLDL treatment was observed. Potassium cyanate did not induce proliferation or DNA synthesis in HCAECs. In conclusion, cLDL produces a profound dysfunction of cultured endothelial cells, which in addition to cell death includes DNA damage and the induction of proliferation.

EXAMPLE 26

CLDL Induces Proliferation of Vascular Smooth Muscle Cells (VSMCs).

Figure 13:
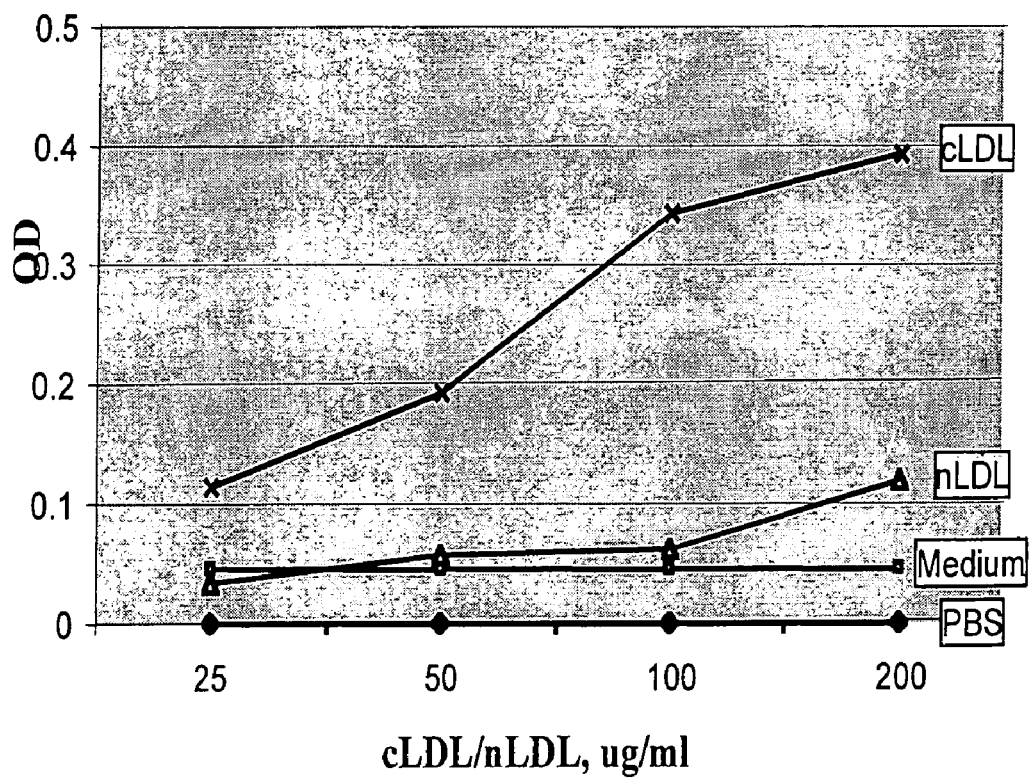
FIG. 13 shows the proliferation of vascular smooth muscle cells in the presence of LDL isoform as measured by a BrdU assay.

Proliferation of vascular smooth muscle cells is a crucial element of the atherosclerotic plaque growth, and thus is very important in the mechanism of atherosclerosis. CLDL induces a significant proliferation of vascular smooth muscle cells in vitro in a dose-dependent manner (FIG. 13).

The following references were cited herein.
1. Reikes S T: Trends in end-stage renal disease. Epidemiology, morbidity, and mortality. *Postgrad Med* 108(1): 124-6, 129-31, 135-136, 2000
2. Venkatesan et al., *Semin Nephrol* 17(4):257-269, 1997
3. Culleton et al., Kidney Int. 56, 2214-2219, 1999
4. Galle et al., *Kidney Int* 55(4):1450-61, 1999
5. Mallat et al., *Br J Pharmacol* 130(5):947-62, 2000
6. Dart et al., *Cardiovasc Res* 43(2):308-22, 1999
7. Kraus et al., *Kidney Int* 59 Suppl 78:S102-7, 2001
8. Steinbrecher et al., *J Lipid Res* 25(10):1109-16, 1984
9. Weisgraber et al., *J Biol Chem* 253(24):9053-62, 1978
10. Trepanier et al., Carbamylation of erythrocyte membrane proteins: an in vitro and an in vivo study. Clin Chem 29(4): 347-355, 1996
11. Yang et al., Inhibitory effect of Chinese green tea on endothelial cell-induced LDL oxidation. Atherosclerosis 2000; 148: 67-73
12. Ueda et al., Proc Natl Acad Sci USA 92:7202-7206, 1995
13. Towbin et al., Proc Natl Acad Sci 76:4350-4354, 1979.
14. Compton et al., Exp Eye Res 40: 297-311, 1985.
15. Roberts et al., Exp Eye Res 50: 157-164, 1990.
16. Lewis B S, Rixon K, Harding J J. Exp Eye Res 43: 973-9, 1986.
17. Nishizawa et al. Am. J. Kidney Dis. 41 (3 Suppl. 1): S76-79, 2003.
18. Apostolov E O et al. Clin. Chem. 2005.
19. Sulowicz et al., Akad. Med. Bialymst. 49: 127-134, 2004.
20. Bambauer R. et al. current topics on low density lipoprotein apheresis. 5: 293-300, 2001.
21. Tani N. Development of selective low-density lipoprotein (LDL) apheresis system: immobilized polyanion as LDL-specific adsorpteion for LDL apheresis system. Artif. Organs. 20: 922-929, 1996.
22. Bambauer R. Artif. Organs. 26: 133-139, 2002.
23. Porkrovsky S. et al. Ther. Apher. Dial. 9: A40, 2005.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:
1. A method of assessing treatment for atherosclerosis, comprising:
   measuring levels of carbamylated low density lipoprotein (cLDL) and/or autoantibody to cLDL in an individual prior to treatment for atherosclerosis;
   measuring levels of cLDL and/or autoantibody to cLDL in said individual after treatment for atherosclerosis; and
   comparing levels of cLDL and/or autoantibody to cLDL in said individual before and after said treatment wherein a decrease in revels of cLDL and/or autoantibody to cLDL after said treatment indicates that the treatment is effective against atherosclerosis.

2. A method of treating an individual by reducing carbamylation of LDL in said individual, comprising:

administering an agent that reduces carbamylation of LDL to said individual thereby reducing carbamylation of LDL; and/or removing cLDL from blood or plasma of said individual.

3. The method of claim 2, wherein the individual is administered an enzymatic carbamylation inhibitor or non-enzymatic carbamylation inhibitor of carbamylation, the individual is administered a monomeric amino acid selected from the group consisting of lysine, glycine, and arginine or the individual is administered an agent that sequesters cLDL in vivo.

4. The method of claim 3, wherein said amino acid is administered in a dose of from about 5 mg/kg to about 500 mg/kg.

5. The method of claim 2, wherein reducing cLDL levels in said individual comprises direct removal of cLDL from blood or plasma of said individual, wherein said direct removal of cLDL comprises:
   (a) passing the blood or plasma of said individual through a dialyzer, wherein said dialyzer comprises immobilized cLDL antibody to bind and remove cLDL; and
   (b) returning the treated blood or plasma back to said individual.

6. The method of claim 5, wherein said cLDL antibody in said dialyzer is immobilized on a dialyzing membrane or on any biocompatible particles.

7. The method of claim 5, wherein said method is combined with hemodialysis of blood or plasmophoresis of plasma.

8. The method of claim 2, wherein said individual is susceptible to atherosclerosis, has renal disease, has advanced renal failure requiring dialysis and/or transplantation or has normal renal function.

\* \* \* \* \*